United States Patent [19]

Schmitt et al.

[11] 4,360,605

[45] Nov. 23, 1982

[54] MIXING COMPONENT FOR DENTAL GLASS IONOMER CEMENTS

[75] Inventors: Werner Schmitt; Robert Purrmann, both of Starnberg; Peter Jochum, Hechendorf; Oswald Gasser, Seefeld, all of Fed. Rep. of Germany

[73] Assignee: Espe Fabrik pharmazeutischer Praparate GmbH, Seefeld, Fed. Rep. of Germany

[21] Appl. No.: 175,389

[22] Filed: Aug. 5, 1980

[30] Foreign Application Priority Data

Aug. 13, 1979 [DE] Fed. Rep. of Germany ....... 2932823

[51] Int. Cl.³ .............................................. C08K 3/40
[52] U.S. Cl. .................................... 523/116; 424/81; 433/228; 524/559
[58] Field of Search ...................... 260/29.6 S, 29.6 H, 260/29.6 BE, DIG. 36, 998.11, 29.6 M; 526/317; 424/81; 523/116; 524/559; 106/33; 433/228

[56] References Cited

U.S. PATENT DOCUMENTS

| | | | |
|---|---|---|---|
| 3,655,605 | 4/1972 | Smith | 260/29.6 S |
| 3,741,926 | 6/1973 | Jurecic | 260/29.6 M |
| 3,882,080 | 5/1975 | Schmitt et al. | 260/29.6 M |
| 3,986,998 | 10/1976 | Schmitt et al. | 260/29.6 M |
| 4,016,124 | 4/1977 | Crisp et al. | 260/29.6 H |
| 4,082,722 | 4/1978 | Schmitt et al. | 260/29.6 S |
| 4,089,830 | 5/1978 | Tezuka et al. | 260/29.6 S |
| 4,106,944 | 8/1978 | Epstein | 260/29.6 S |
| 4,123,416 | 10/1978 | Porter et al. | 260/42.18 |
| 4,154,717 | 5/1979 | Kohmura et al. | 260/29.6 M |
| 4,174,334 | 11/1979 | Bertenshaw et al. | 260/29.6 S |

FOREIGN PATENT DOCUMENTS

909414 9/1972 Canada .
1504520 3/1978 United Kingdom .
1504708 3/1978 United Kingdom .

OTHER PUBLICATIONS

Derwent Abst. 20230A/11 "Aq. Hardening Soln. for Dental Cement . . . "(J53010590) G. C. Shika Kogyo KK (NIPK) 1-31-78.

*Primary Examiner*—Melvyn I. Marquis
*Assistant Examiner*—Herbert J. Lilling
*Attorney, Agent, or Firm*—Bacon & Thomas

[57] ABSTRACT

Dental glass ionomer cements are obtained by using as a mixing component for preparing the final cement mixture either a liquid mixing component comprising an aqueous solution of a certain maleic acid-acrylic acid-copolymer and optionally usual additives or a solid, powdery mixing component comprising a powder mixture of a glass ionomer cement powder and the maleic acid-acrylic acid-copolymer in solid form and optionally usual additives.

10 Claims, 1 Drawing Figure

Adhesive Strength of Dental Cements

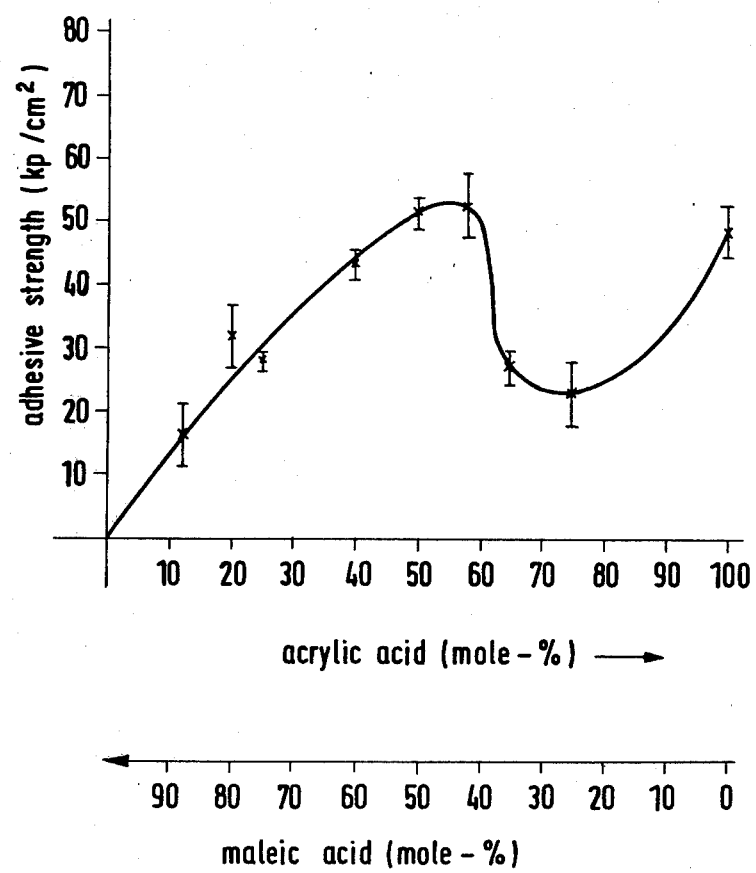

MIXING COMPONENT FOR DENTAL GLASS IONOMER CEMENTS

BACKGROUND OF THE INVENTION

During recent years in the dental field, cements which are formed from an inorganic powdery component and an organic polymer comprising carboxylic acid groups have achieved increased importance as filling materials for teeth as well as for fixing materials.

Carboxylate cements formed from zinc oxide and an aqueous polyacrylic acid solution are known, for example, from German Auslegeschrift No. 16 17 688. Although they are physiologically compatible, they are not suitable as permanent filling materials for aesthetic reasons where they are visible. Further, they show only moderate mechanical strength. Advantageous, however, is that they are chemically bound to the tooth enamel and to dentin. Thus carboxylate cements are broadly used as linings in a tooth cavity and as fixing cements.

It is known from Czechoslovakian certificate of authorship, No. 156 804, that the mechanical strength of the above described cements which are formed from zinc oxide or a mixture of zinc oxide and magnesium oxide may be improved by using an aqueous solution of a copolymer of acrylic acid with 0.1 to 50% of another unsaturated carboxylic acid or an anhydride thereof as a mixing component. While the thus formed cements show improved strength, the aesthetic drawbacks still are the same as those of a conventional zinc oxide polyacrylic acid system.

Permanent filling materials for dental use which show an excellent aesthetic effect together with high strength are the so-called silicate cements which are formed from a silicate glass powder and an aqueous solution of phosphoric acid.

A disadvantage of the silicate cements is that they are harmful to the dental pulp and are relatively soluble under oral conditions. The former weakness is particularly serious; it necessitates the application of cavity lining agents, procedures which are time consuming and in many cases unreliable.

Compared with the above-described silicate cements a remarkable improvement was achieved by the development of the so-called glass ionomer cements, which not only have favourable aesthetic and mechanical characteristics, but also are satisfying concerning their physiological compatibility. A cement system of that type is described in German Offenlegungsschrift No. 21 01 889. By using aqueous solutions of polymers derived from unsaturated $\alpha,\beta$-dicarboxylic acids having four or five carbon atoms as a mixing liquid there is obtained a dental cement which shows an excellent setting performance, good strength, a good physiological compatability and a satisfying aesthetic appearance.

A surview of this field is provided in the article of A. D. Wilson in "Chemical Society Reviews", 7 (2), p. 265 to 296 (1978).

Still further cement systems having a powder component consisting of a metal oxide powder, such as zinc oxide, or a silicate cement powder, are known from German Auslegeschrift No. 24 39 882. As a mixing liquid for these cements there are used aqueous solutions of acrylic acid-itaconic acid-copolymers in which the preferred ratio of acrylic acid units to itaconic acid units is in the range of 91:1 to 2:1. Further, British Pat. No. 1,382,881 describes glass ionomer cement systems having a mixing component consisting of an aqueous solution of copolymers of unsaturated $\alpha,\beta$-dicarbocylic acids, which contain more than 50 mole % of unsaturated $\alpha,\beta$-dicarbocylic acid units. As specific examples for polymers in this patent maleic acid-itaconic acid-copolymers and copolymers of maleic acid and acrylic or methacrylic acid, comprising more than 90% of maleic acid units are stated.

In spite of their above described aesthetic and physiological advantages these cements still need to be improved, because their adhesion to the tooth enamel and to dentin is still insufficient. While a better adhesion could be achieved by the use of an aqueous polyacrylic acid solution as a mixing component, in such a case, however, the favourable setting characteristics of the cements would be lost.

SUMMARY OF THE INVENTION

The invention relates to dental glass ionomer cements. More particularly, this invention relates to a mixing component for glass ionomer cements, by which a cement is obtained which not only has a good mechanical strength and favourable setting characteristics, but is satisfying in aesthetic and cosmetic respect and has such a good physiological behaviour that it may be used for filling a cavity in a tooth without using a cavity lining agent or similar precautions and, furthermore, has an excellent adhesion to the tooth enamel and to dentin.

DESCRIPTION OF THE PREFERRED EMBODIMENTS

The object of this invention is achieved by using in the preparation of glass ionomer cements a maleic acid-acrylic acid-copolymer having a specifically selected composition.

According to the invention a mixing component for glass ionomer cements is provided, which may be a liquid mixing component (case a) and in such case consists of an aqueous solution comprising 20 to 65% by weight of a maleic acid-acrylic acid-copolymer and optionally further contains usual additives or may be a solid mixing component (case b) and, in such case, consists of a powder mixture of a glass ionomer cement and a maleic acid-acrylic acid-copolymer, optionally with usual additives. The invention is characterized in that the copolymer consists of 20 to 65 mole % acrylic acid units and 80 to 35 mole % maleic acid units.

Considering the above described prior art, it was surprising that acrylic acid-maleic acid-copolymers having the above defined range of composition show especially improved adhesive strength to the dentin and enamel. According to the prior art when using polymaleic acid as a mixing component for glass ionomer cements there is obtained a cement which shows unsatisfactory adhesive strength to the dentin and enamel.

The use of an aqueous solution of polyacrylic acid as a mixing component for silicate cements provides a sufficient adhesive strength, but in such a case a system is obtained which has unfavourable setting characteristics. If it is attempted to incorporate a slight amount of maleic acid units into the acrylic acid polymer the adhesion of the thus formed cements is drastically deteriorated.

It was therefore quite unexpected that by using maleic acid-acrylic acid-copolymers within the range of higher concentrations of maleic acid units, to the contrary, there can be obtained a maximum of the adhesive strength between the cement and the tooth enamel and the dentin.

The FIGURE of the accompanying drawing diagrammatically shows the favourable effect achieved by the mixing component according to the invention. The curve illustrates the degree of adhesion achieved in relation to the composition of the copolymer.

The points shown in the diagram of the drawing, on which the curve is based, were obtained as averages in a test series by using test bodies which had been stored for one hour at 36° C. and at a relative humidity of 100% and for 20 hours in water of 36° C. respectively. It may be seen from the diagram that maleic acid-acrylic acid-copolymers having a low content of acrylic acid units, as well as those having a high ratio of acrylic acid units show a lower adhesive strength than those copolymers containing acrylic acid units in an intermediate range. Copolymers having a composition within the specific range of 20 to 65 mole % acrylic acid units lead to the formation of cement systems having an excellent adhesive strength.

Especially preferable, according to the invention, are those copolymers which contain about 40 to 60 mole % acrylic acid units and about 60 to about 40 mole % maleic acid units.

The molar ratio, in any case, is to be understood as the average of all individual molecules of the copolymer.

Compared with mixing components comprising acrylic acid-itaconic acid-copolymers (known from German Auslegeschrift No. 24 39 882) the mixing components according to the invention show a remarkably improved compressive strength which may be shown by a comparative example described later.

Processes for preparing the copolymers used according to the invention are known; such a process for example is described in German Offenlegungsschrift No. 22 12 632 (example 3) and in the article by A. A. El'Saied et al, Polym. Sci. USSR, 11, 314 (1969).

The average molecular weight of copolymers useful for the invention may be characterized by their viscosity in aqueous solutions. If the polymer concentration of an aqueous solution is 43%, the viscosity of the aqueous solution is in the range of 0.5 to 1000 Poises, preferably 1 to 100 Poises and more preferably 3 to 50 Poises (each value measured at 25° C.).

Copolymers having the shown composition may be used for the invention after a usual purification step.

Generally, binary copolymers consisting of acrylic acid and maleic acid units may be used, the copolymers however may also contain minor amounts of additional comonomer units provided that these do not change the characteristics of the copolymer and further provided that the above-defined molar ratio of 20 to 65 molar amounts acrylic acid units to 80 to 35 molar amounts maleic acid units is maintained.

The powder component of the cement system according to the invention may be a conventional silicate cement powder such as described in German Offenlegungsschrift No. 21 01 889. On the other hand, the mixing component of the invention is specifically favourable in combination with calcium aluminum fluorosilicate glass powders which are described in German Offenlegungsschrift No. 20 61 513. Useful silicate cement powders further are stated in "Chemical Society Reviews", 7 (2), p. 265 to 296 (1978).

Conventionally, dental cements are used in the form of a two component system consisting of a liqudid component and a solid powder component.

The mixing component according to the invention according to one embodiment (a) may be part of the mixing liquid, while according to another embodiment (b) it may be part of the powder component.

Case (a). According to the former case the mixing liquid consists of an aqueous solution of the above defined maleic acid-acrylic acid-copolymer, optionally together with conventional additives.

If the cement system is to be used as a cement for filling tooth cavities, the aqueous solution generally contains the copolymer in a concentration of at least 20% by weight, preferably 3 to 60% by weight and more preferably 40 to 50% by weight. For the use as a fixing cement and for prosthetic purposes also lower concentrations are useful.

The copolymer solutions should have a viscosity of at least 0.5 poise, however, not more than 300 Poises. The preferred range of viscosity is between 2 and 200, particularly between 5 and 100 poise at 25° C.

It is customary to sell dental preparations predosed in so-called shaking caps. Liquid and powder are kept in two separate compartments and combined and mechanically mixed immediately before use. This predosing is also applicable to the mixing component according to the invention.

Case (b). According to another preferred embodiment of the invention the mixing component, i.e., the maleic acid-acrylic acid-copolymer forms part of the powder mixture and is present as a pre-mix consisting of silicate cement powder and maleic acid-acrylic acid-copolymer in solid form. For forming the final cement system the powder component then may be mixed with water, optionally together with conventional additives.

In both cases usual additives such as chelating agents, preferably tartaric acid, may be incorporated into the powder component and/or into the liquid component in order to improve the setting characteristic (German Offenlegungsschrift No. 23 19 715). The addition of tartaric acid has no influence on the adhesion of the resulting cement to the tooth enamel and dentin.

Further, other usual additives, such as fluorides, bacteriostatic agents of antibiotics, etc. may be added to the liquid or to the powder component in minor amounts and the powder compound may further contain usual pigments.

Various intermediaries are possible in between the two embodiments (a) and (b) thus, e.g., half of the copolymer according to the invention can be added to the liquid and half to the powdery mixing component.

Also in case of the latter embodiment (b) it may be useful to provide and sell the preparation predosed in shaking caps. It may further be especially preferable to compress the powder mixture to form a tablet.

The adhesive strength of dental cements which are prepared by means of the mixing component according to the invention was measured according to the following procedure:

A cow's tooth is faced and the enamel layer is polished and kept free of fat. The tooth is embedded in plaster and the treated surface is adjusted in a plane parallel to the measuring table. The calcium aluminum-fluoro-silicate glass powder is pasted with the approximately 44% aqueous solution of the respective copolymer in a weight ratio of about 3.0:1. A steel cylinder of a length of 30 mm. and diameter of 8 mm. is filled with this cement composition. At a distance of 3 mm. from the inlet opening a wire of 1 mm. diameter is inserted by bores in order to provide a more suitable retention of the filling cement within the cylinder.

By means of a guide, which guarantees a vertical positioning, the steel cylinder is placed on the plane tooth surface and loaded for 10 min. with a mass of 100 g.

The teeth carrying the bodies that are to be drawn off are stored in the following manner:

10 min. at ambient temperature, 1 hour at 100% air humidity and 36° C., 20 hours under water at 36° C.

After storing, the steel cylinder is drawn off with an advance of 4 mm. per minute on a suitable testing machine. The force required for drawing off the steel cylinder is recorded and shows upon multiplication with the factor 3.5 the adhesion in kiloponds per $cm^2$. The said measuring is effected with the same cement composition on 5 different teeth and the average is calculated therefrom.

The values measured by this method on materials according to the invention are plotted as in the figure of the attached drawing.

The measuring of the viscosity of the copolymer solution was effected with the aid of a rotational viscosimeter. For this purpose an apparatus, identified by the name HAAKE ROTO VISKO, with a rotating body HV I, gear number 3, engine speed number 1 and calibration constant 48.5 was used. The absolute viscosity in Centiposes is obtained by multiplication of the scale reading with said three parameters.

The invention is explained in more detail by the following examples, but should not be regarded as being restricted by them. In these examples 10% by weight of tartaric acid is added to all mixing liquids, if not otherwise indicated.

EXAMPLE 1

An acrylic acid-maleic acid-copolymer (molar ratio 3:2), suitable for dental medical purposes is mixed with water to a concentration of about 43% by weight. The solution has a viscosity of 12 poise/25° C. This liquid is mixed with a commercial silicate cement powder (Syntrex) in a weight ratio of 1:2.5, to obtain a paste that is well suitable for clinical purposes. The paste is introduced in known manner into prepared tooth cavities. The mixture hardens after a few minutes and has in the set state a transparency corresponding to the natural tooth. The filling shows good adhesion to the cleaned tooth substance, even if the usual mechanical retentions are not prepared.

EXAMPLE 2

A copolymer having a molar ratio of maleic acid:acrylic acid of 1:1 is used according to example 1 to prepare a mixing liquid for dental cements. A commercial glass ionomer cement powder (G.C.'s Fuji) is mixed with this liquid in a weight ratio of 2.3:1 to form a paste. The thus obtained cement is useful as a filling material for tooth cavities. The adhesive strength to the tooth enamel amounts to 50 kp per $cm^2$. The compressive strength is 1.860 $kp/cm^2$.

EXAMPLE 3

The copolymer of example 2 is dissolved in water to form an aqueous solution of a concentration of 35% by weight (viscosity: 3 poise/25° C.). After this liquid has been mixed with commercial glass ionomer cement powder for fixing use (De Trey Chem-Bond), in a powder-liquid-ratio of 1.2:1, a thin-flowing cement is obtained which shows good adhesion to the tooth substance and has a compressive strength of 1.100 kp per $cm^2$.

EXAMPLE 4

240 mg-portions of a commercial glass ionomer cement powder (ASPA) are filled into the mixing compartment of shaking caps according to German Offenlegungsschrift No. 19 10 885. As a separate compartment this capsule contains a foil bag from plastic covered aluminum, which is filled with 96 mg of the copolymer solution described in example 1. When such a filled capsule is used, as described in DE-OS No. 19 10 885, after mixing by means of a mechanical mixing device a cement is obtained which is useful as a permanent filling material for tooth cavities (specifically for cervical lesions) and which has a good adhesive strength to the tooth substance.

EXAMPLE 5

A dry intimate mixture from 300 mg commercially available glass ionomer cement powder (ASPA) and 41 mg of the copolymer mentioned in example 2 is compressed in the usual manner to form a tablet. After short wetting of this tablet in 59 mg of a 14% tartaric acid solution the tablet may easily be mixed to form a cement paste which is well suited for filling cervical lesions and shows good adhesive strength to the tooth substance.

EXAMPLE 6

The same dry powder mixture as stated in example 5 (371 mg) is filled into the mixing chamber of a shaking cap according to DE-OS No. 19 10 885. This cap comprises a foil bag consisting of plastic coated aluminum as a separate container, which is filled with 63 mg of a 15% aqueous tartaric acid solution. After a further processing as described in Example 4 there is obtained a filling materal with self-adherence to the tooth substance having good compressive strength.

COMPARATIVE EXAMPLE

This example shows that according to the invention the compressive strength is improved over a known polycarboxylate cement based on acrylic acid-itaconic acid-copolymers.

Commercially available glass ionomer cement powder (De Trey, ASPA) was mixed to form a paste with the corresponding mixing liquid in a powder/liquid-ratio of 3.0/1. The thus obtained cement mixture was shaped in suitable molds to form cylindrical bodies having a length of 8 mm. and diameter of 4 mm. The bodies were kept at 100% relative humidity for 24 hours and then used for measuring the compressive strength.

| RESULTS | |
|---|---|
| Mixing Liquid | Compressive Strength |
| Acrylic acid-itaconic acid-copolymer (De Trey, ASPA liquid) | 1320 $kp/cm^2$ |
| According to the invention, acrylic acid-maleic acid-copolymer (molar ratio 1:1) | 1680 $kp/cm^2$ |

It may be seen from the results that the compressive strength of the cement prepared by using a mixing liquid according to the invention is about 25% higher than that obtained with the known mixing liquid.

We claim:

1. A two component mixing preparation for glass ionomer cements selected from the group consisting of:
   (a) a glass ionomer cement powder and an aqueous solution containing from about 20 to 65% by weight of a maleic acid-acrylic acid copolymer which contains from 20 to 65 mole % acrylic acid units and from 80 to 35 mole % maleic acid units, and
   (b) a powder mixture of a glass ionomer cement powder and a maleic acid-acrylic acid copolymer in solid form which contains from 20 to 65 mole % acrylic acid units and from 80 to 35 mole % maleic acid units.

2. A mixing preparation according to claim 1 (a) characterized in that the copolymer is dissolved in a concentration of from 30 to 60% by weight in the aqueous solution.

3. A mixing preparation according to claim 1 or 2, characterized in that the copolymer contains 40 to 60 mole % acrylic acid units and 60 to 40 mole % maleic acid units.

4. A solid mixing preparation according to claim 1 (b) or 3, characterized in that the powder mixture comprising the glass ionomer cement powder and the maleic acid-acrylic acid copolymer is compressed in the shape of a tablet.

5. A mixing preparation according to claim 1 or 2 containing a minor amount of at least one additive selected from the group consisting of chelating agents, fluorides, bacteriostatic agents, antibiotics and pigments.

6. A mixing preparation according to claim 5 containing tartaric acid as a chelating agent.

7. A mixing preparation according to claim 1 (a), wherein the copolymer solution has a viscosity between 2 and 200 poise at 25° C.

8. A method of preparing a glass ionomer cement comprising of mixing an aqueous solution containing from about 20 to 65 percent by weight of a maleic acid-acrylic acid copolymer which contains from 2 to 65 mole % acrylic acid units and from 80 to 35 mole % maleic acid units with a glass powder to form a paste, forming the paste into the desired shape and permitting it to set.

9. A method for preparing a glass ionomer cement comprising of mixing a powder mixture of a glass component and a maleic acid-acrylic acid copolymer which contains from 20 to 65 mole % acrylic acid units and from 80 to 35 mole % maleic acid units with water to form a paste, forming the paste into the desired shape and permitting it to set.

10. The method of claim 8 or 9 wherein the paste is introduced into a prepared tooth cavity and is permitted to set.

* * * * *